United States Patent
Rizkalla

(10) Patent No.: US 8,791,280 B2
(45) Date of Patent: Jul. 29, 2014

(54) PROCESS FOR PREPARATION OF CATALYST CARRIER AND ITS USE IN CATALYST PREPARATION

(75) Inventor: Nabil Rizkalla, Riverdale, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 829 days.

(21) Appl. No.: 11/201,030

(22) Filed: Aug. 10, 2005

(65) Prior Publication Data

US 2007/0037991 A1    Feb. 15, 2007

(51) Int. Cl.
| | |
|---|---|
| *C07D 301/10* | (2006.01) |
| *C07D 301/03* | (2006.01) |
| *B01J 23/50* | (2006.01) |
| *B01J 21/04* | (2006.01) |
| *B01J 23/00* | (2006.01) |
| *B01J 31/00* | (2006.01) |

(52) U.S. Cl.
USPC .......... 549/533; 549/512; 549/518; 549/523; 549/532; 502/252; 502/302; 502/152; 502/230; 502/355; 502/257; 502/313; 502/333; 502/439; 502/72; 502/154; 502/159; 502/168; 502/178; 502/204; 502/208; 502/213; 502/220; 502/225; 502/242; 502/263; 502/303; 502/316; 502/325; 502/341

(58) Field of Classification Search
USPC .......... 208/122, 138, 143, 213, 89; 585/443, 585/310; 564/469, 480; 502/252, 302, 66, 502/152, 230, 257, 313, 333, 439, 65, 154, 502/159, 168, 178, 204, 208, 213, 220, 225, 502/242, 263, 303, 316, 325, 341, 72, 355; 549/512, 518, 523, 532, 533
See application file for complete search history.

(56) References Cited

U.S. PATENT DOCUMENTS

| | | | |
|---|---|---|---|
| 3,172,866 A | 3/1965 | Belon | |
| 3,664,970 A * | 5/1972 | De Maio | 502/243 |
| 4,022,715 A | 5/1977 | Bornfriend | 252/463 |
| 4,260,524 A | 4/1981 | Yamada et al. | |
| 4,379,109 A * | 4/1983 | Simpson | 156/89.22 |
| 4,631,267 A * | 12/1986 | Lachman et al. | 502/439 |
| 4,874,739 A * | 10/1989 | Boxhoorn | 502/218 |
| 5,380,697 A * | 1/1995 | Matusz et al. | 502/348 |
| 5,384,302 A | 1/1995 | Gerdes et al. | |
| 5,733,842 A * | 3/1998 | Gerdes et al. | 502/439 |
| 5,739,075 A * | 4/1998 | Matusz | 502/302 |
| 5,929,259 A | 7/1999 | Lockemeyer | |
| 6,342,191 B1 * | 1/2002 | Kepner et al. | 423/210 |
| 6,677,261 B1 * | 1/2004 | Addiego et al. | 501/127 |
| 2004/0259718 A1 | 12/2004 | Feige et al. | |

FOREIGN PATENT DOCUMENTS

| | | |
|---|---|---|
| EP | 0 716 886 A2 | 6/1996 |
| WO | WO 2007/021473 A2 | 2/2007 |

OTHER PUBLICATIONS

Extended Search Report dated Feb. 4, 2011 and Supplementary Search Report dated Jan. 28, 2011 received from the European Patent Office.

* cited by examiner

*Primary Examiner* — Elizabeth Wood
(74) *Attorney, Agent, or Firm* — Scully, Scott, Murphy & Presser, P.C.

(57) ABSTRACT

This invention relates to catalyst carriers to be used as supports for metal and metal oxide catalyst components of use in a variety of chemical reactions. More specifically, the invention provides a process of formulating an alpha alumina carrier that is suitable as a support for silver and the use of such catalyst in chemical reactions, especially the epoxidation of ethylene to ethylene oxide. The composition comprises at least one hydrated precursor of alpha alumina; an optional alpha alumina; and a binder. The composition is substantially free of seeding particles.

21 Claims, No Drawings

PROCESS FOR PREPARATION OF CATALYST CARRIER AND ITS USE IN CATALYST PREPARATION

BACKGROUND OF THE INVENTION

1. Field of the Invention

This invention relates to catalyst carriers to be used as supports for metal and metal oxide catalyst components which are then used in a variety of chemical reactions. More specifically, the invention pertains to a process of formulating catalyst having a low surface area alpha alumina carrier that is suitable as a support for silver, and the use of such catalyst in chemical reactions, especially the epoxidation of ethylene to ethylene oxide.

2. Description of the Related Art

Alumina is well known to be useful as a catalyst support for the epoxidation of olefins. It is particularly useful as a support for a catalyst comprising silver which is employed in the oxidation of ethylene to ethylene oxide. Support materials are made by fusing high purity aluminum oxide, with or without silica. For this purpose the support material often comprises 90 percent or more, by weight, alpha alumina and up to 6 percent, by weight, silica. They are usually very porous and have a high or low surface area depending on the use to be made of them.

In known processes of making a support, alpha alumina and/or transition alumina (alpha alumina precursors) is thoroughly mixed with temporary and permanent binders. The temporary binders hold together the components of the carrier precursor during its processing. The permanent binders are inorganic materials having fusion temperatures below that of the alumina and induce fusion at the points of contact of the alumina particles, and impart mechanical strength to the finished support. After thorough dry-mixing, sufficient water is added to the mass to form the mass into a paste-like extrudable admixture. The catalyst support particles are then formed from the paste by conventional means such as high pressure extrusion, tableting, granulation or other ceramic forming processes. The particles are then dried and are subsequently fired at an elevated temperature.

In the firing step, the temporary binders are burnt or thermally decomposed to carbon dioxide and water, and are volatilized. It is known in the art that ceramic carrier based catalysts comprise inert, solid supports such as alpha alumina. Such have been described in U.S. Pat. Nos. 3,664,970; 3,804,781; 4,428,863 and 4,874,739. U.S. patents which describe the making of alumina supports include U.S. Pat. Nos. 2,499,675; 2,950,169 and 3,172,866. Such carriers have potential applications in the catalytic field especially where the alumina base is alpha alumina. Other patents such as U.S. Pat. Nos. 3,222,129; 3,223,483 and 3,226,191 show the preparation of active aluminas. Methods of making highly porous aluminas are disclosed in U.S. Pat. Nos. 3,804,781; 3,856,708; 3,907,512 and 3,907,982. Alumina carriers having high thermal stability are disclosed in U.S. Pat. No. 3,928,236. Other methods of making catalyst carriers are discussed in U.S. Pat. Nos. 3,987,155; 3,997,476; 4,001,144; 4,022,715; 4,039,481; 4,098,874 and 4,242,233. U.S. Pat. No. 3,664,970 discloses a carrier containing mainly alumina and also contains silica, magnesia and titania. U.S. Pat. No. 4,410,453 discloses that the performance of a silver on alumina catalyst for the oxidation of ethylene to ethylene oxide is improved by the inclusion of an oxide, or oxide precursor, of zinc, lanthanum, or magnesium. U.S. Pat. No. 4,200,552 discloses a carrier that is made of $\alpha$-alumina and at least one of the compounds $SiO_2$, $TiO_2$, $ZrO_2$, CaO, MgO, $B_2O_3$, $MnO_2$, or $Cr_2O_3$, as a sintering agent. U.S. Pat. No. 4,455,392 discloses the composition of an alumina carrier that contains silica and magnesia as components of the bonding material. U.S. Pat. No. 5,100,859 discloses a carrier that contains an alkaline earth metal silicate, which may be added as an original component or generated in situ by the reaction of silica, or silica generating compounds, with compounds that decompose to alkaline earth metal oxide upon heating. U.S. Pat. No. 5,512,530 discloses a process for the production of a catalyst carrier which is based on mixing alpha alumina, burnout material, and titania. U.S. Pat. No. 5,380,697 discloses a carrier containing a ceramic bond comprises 60% wt. silica, 29% wt. alumina, 3% wt. calcium oxide, 2% magnesia, 4% wt. alkali metal oxides and less than 1% wt. each of ferric oxide and titania. U.S. Pat. No. 5,733,840 and U.S. Pat. No. 5,929,259 disclose a titania-modification of formed carriers. The treatment involved impregnating the pre-formed carrier with a solution of titanyl oxalate, titanium (IV) bis(ammonium lactato)dihydroxide, or similar organic salts and then the impregnated carrier is calcined at a temperature from about 450 to 700° C. The patents disclosed that if titania is added during the carrier's preparation, it tend to affect the densification of the carrier structure which can lead to unacceptable properties. U.S. Pat. No. 4,368,144 states that better catalytic performance was obtained with carriers that contain no more than 0.07% Na. U.S. Pat. No. 6,103,916 patent discloses that catalyst performance was improved when the carrier was washed by boiling in pure water until the water resistivity is more than 10,000 $\Omega \cdot$cm. U.S. Pat. No. 5,384,302 patent disclosed an $\alpha$-alumina based carrier which prepared by mixing at least two alumina components. The first provides 95-40% of the total aluminum components and is made of $\alpha$-alumina of crystallite size of 0.4-4µ.

One of the problems with the catalysts that are based on porous carriers is that they have an insufficiently uniform pore structure. U.S. Pat. No. 4,022,715 attempts to solve this problem by using an organic solution of a blowing agent, mixed with a carrier precursor composition. It has now been found that an improved carrier pore structure can be formed by employing a composition for a catalyst support which comprises an admixture of a transition alumina alone with or without an alpha alumina having a median particle size of about 5µ or greater; and a binder. The composition is substantially free of seeding particles. Optionally the composition may have either a solid blowing agent which expands, or propels a gas upon the application of sufficient heat, talc and/or a water soluble titanium compound.

The catalyst support of this invention has excellent crush strength, porosity, and surface area on which the catalytic component will be deposited. The optimum porosity and surface area are important for catalytic function and insures the absence of diffusional resistances for reactants and product gases under reaction conditions. A minimum surface area is important because it provides the structure on which the catalytic component will be deposited. Crush strength is a parameter of the physical integrity of the carrier. This physical strength is essential for the catalyst ability to withstand handling as well as its long life in a commercial reactor. A carrier that has the optimum surface area and porosity may be deficient in its crush strength, and vice versa. The balance between the different physical specifications of the carrier is important. Normally, a carrier that has the optimum surface area and porosity may be deficient in its crush strength, and visa-versa. The proper choice of the specifications of the alpha alumina, that is used in the carrier composite, will help in the balance between the properties of the finished carrier.

An optimum balance between these specifications is obtained via the choice of the carrier components according to the invention.

SUMMARY OF THE INVENTION

One embodiment of the invention provides a composition for producing a catalyst support which comprises an admixture of at least one alpha alumina having a median particle size of about 5μ or greater, in an amount of from about 20 percent to about 60 percent by weight of total alumina in the composition; at least one hydrated precursor of alpha alumina in an amount of from about 40 percent to about 80 percent by weight of total alumina in the composition; and a binder; which composition is substantially free of seeding particles.

Another embodiment of the invention provides a process for producing a catalyst support which comprises:
a) preparing composition for producing a catalyst support which comprises an admixture of at least one alpha alumina having a median particle size of about 5μ or greater, in an amount of from about 20 percent to about 60 percent by weight of total alumina in the composition; at least one hydrated precursor of alpha alumina in an amount of from about 40 percent to about 80 percent by weight of total alumina in the composition; and a binder; which composition is substantially free of seeding particles; thereafter
b) molding the resultant composition into a structure; thereafter
c) heating said structure for a sufficient time and at a sufficient temperature to form a porous structure, and thereafter
d) heating the porous structure for a sufficient time and at a sufficient temperature to convert transition alumina, to alpha alumina, and form a porous alpha alumina structure, and to fuse the porous structure and thereby form a catalyst support.

Another embodiment of the invention provides a process for producing a catalyst support which comprises:
a) preparing composition for producing a catalyst support which comprises at least one hydrated precursor of alpha alumina; and a binder; which composition is substantially free of alpha alumina, and substantially free of seeding particles; thereafter
b) molding the resultant composition into a structure; thereafter
c) heating said structure for a sufficient time and at a sufficient temperature to form a porous structure, and thereafter
d) heating the porous structure for a sufficient time and at a sufficient temperature to convert the hydrated precursor of alpha alumina, to alpha alumina, and form a porous alpha alumina structure, and to fuse the porous structure and thereby form a catalyst support.

DETAILED DESCRIPTION OF THE INVENTION

A first embodiment of the invention provides a composition for producing a catalyst support which comprises an admixture of at least one alpha alumina having a median particle size of about 5μ or greater, in an amount of from about 20 percent to about 60 percent by weight of total alumina in the composition; at least one hydrated precursor of alpha alumina in an amount of from about 40 percent to about 80 percent by weight of total alumina in the composition; and a binder; which composition is substantially free of seeding particles. In this embodiment, the alpha alumina is preferably present in an amount of from about 40 percent to about 60 percent by weight of total alumina in the composition. In this embodiment, the at least one hydrated precursor of alpha alumina in an amount of from about 40 percent to about 60 percent by weight of total alumina in the composition. In the context of this invention, seeding particles are those which produce nucleation sites for the formation of alpha alumina from the hydrated precursor.

In another embodiment of the invention, the composition for producing a catalyst support which comprises at least one hydrated precursor of alpha alumina; and a binder; which composition is substantially free of alpha alumina, and substantially free of seeding particles.

The hydrated precursor of alpha alumina may comprise an aluminum hydroxide such as gibbsite, boehmite, diaspore, bayerite and combinations thereof. The total amount of alumina, that is alpha alumina plus hydrated precursor of alpha alumina (transition alumina) may be present in the composition in an amount of from about 80 weight % to about 100 weight % based on the weight of the finished carrier. It is preferably present in an amount of from about 90 weight % to about 99 weight % based on the weight of the finished carrier, more preferably from about 97 weight % to about 99 weight percent based on the weight of the finished carrier. Preferably the composition is substantially free of ferric oxide, chromium oxide, and sub-micron size particles of alpha alumina.

The composition is prepared by forming a physical admixture of the composition components. The binder may be a temporary binder, a permanent binder, or both. The temporary binders are thermally decomposable organic compounds of moderate to high molecular weight. The permanent binders are inorganic clay-type materials that impart mechanical strength to the finished support.

Temporary binders, and burnout materials, include thermally decomposable organic compounds, polyolefin oxides, oil, e.g. mineral oil, acacia, carbonaceous materials such as coke, carbon powders, graphite, cellulose, substituted celluloses, e.g. methylcellulose, ethylcellulose, and carboxyethylcellulose, cellulose ethers, stearates, such as stearate esters, e.g. methyl or ethyl stearate, waxes, powdered plastics such as polyolefins, particularly polyethylene and polypropylene, polystyrene, polycarbonate, sawdust, starch, and ground nut shell flours, e.g. pecan, cashew, walnut and filbert shells, and combinations thereof, and the like which burn at the firing temperatures employed. Burnout material is used primarily to ensure the preservation of the structure during the green, or unfired phase, in which the mixture may be shaped into particles by molding or extrusion processes and also provide the desired porosity to the finished product. When employed, a temporary binder is essentially totally removed during the firing to produce the finished support. The supports of the invention are preferably made with the inclusion of a permanent binder material to ensure preservation of the porous structure and to give added strength to the carrier after the carrier is fired. Permanent binders, include inorganic clay materials, silica, alkaline earth metal oxides, alkali metal oxides, and titanium oxide, silicates of elements of Group II of the Periodic Table of the elements, and combinations thereof. Useful clays non-exclusively include kaolinite. A convenient binder material which may be incorporated with the alumina particles is a mixture of boehmite, stabilized silica sol and a soluble sodium salt. Suitable bond materials for this invention include calcium silicate and magnesium silicate either added as such or formed in situ. It is preferred, however, to use no free alkali metals, or their oxides. The binder may be present in the precursor in an amount of from about 0.1 weight % to about 15 weight % based on the weight of the composition, preferably from about 0.2 weight % to about 10 weight % based on the weight of the composition, and more preferably from about 0.5 weight % to about 5 weight % based on the weight of the composition.

The composition may optionally contain a solid blowing agent which expands, or propels a gas upon the application of sufficient heat. In one embodiment, the blowing agent comprises a composition of microspheres which include thermoplastic shells which encapsulate a hydrocarbon. The hydrocarbon expands the thermoplastic shells upon the application of sufficient heat. Such blowing agents comprise gas-tight thermoplastic shells that may encapsulate a hydrocarbon in liquid form. Upon heating, the hydrocarbon is gasified and increases its pressure while the thermoplastic shell softens, resulting in an increase in the volume of the microspheres. Examples of expandable microspheres are Advancell, acrylonitrile-based spheres, commercially available from Sekisui Chemical Co. (Osaka, Japan) and Expancel® microspheres, commercially available from Expancel, Stockviksverken, Sweden. Expancel is available in unexpanded and expanded microsphere forms. Unexpanded microspheres have a diameter of from about 6 to about 40 µm, depending on grade. When heated, these microspheres expand to from about 20 to about 150 µm in diameter. The preferred hydrocarbon inside the shell is isobutane or isopentane. The shell is preferably a copolymer of monomers, e.g. vinylidene chloride, acrylonitrile and methyl methacrylate. In another embodiment, the blowing agent may be a solid, granular chemical blowing agent which decomposes upon heating, releasing a considerable amount of gaseous decomposition products and resulting in pore formation. Chemical blowing agents are preferably solid forms of hydrazine derivatives that will release gases such as $CO_2$ and nitrogen. Examples of chemical blowing agents are p-toluenesulfonylhydrazide, benzenesulfonylhydrazide, and azodicarbonamide, $H_2NCO-N=N-CONH_2$. Azodicarbonamide decomposes at 200° C., into $N_2$, CO, and $CO_2$.

A suitable amount of blowing agent to provide the desired porosity may be in the range of from about 0.1 weight % to about 30 weight % by weight of the overall composition. Preferably, the amount of the blowing agent ranges from about 1 weight % to about 20 weight % and more preferably from about 3 weight % to about 15 weight percent based on the weight of the composition. The amount of blowing agent is a function of its type, the type of alpha alumina and/or a transition alumina components used, as well as the nature of the porosity that is desired in the finished product.

After thorough dry-mixing of the alpha alumina, hydrated precursor of alpha alumina material, binder and optional blowing agent, sufficient water is added to the precursor mass to form a paste-like substance. Water and/or a water-containing substance is added to the starting precursor in order to give plasticity to the mixture. The plastic mixture is then formed into the desired shape via standard ceramic processing methods, e.g. tableting or extrusion. The amount of water added to the carrier precursor will be a function of the method used to form the paste. Extrusion may require the addition of a higher level of water to gain the optimum level of plasticity. Where particles are formed by extrusion it may be desirable to include conventional extrusion aids such as lubricants, for example petroleum jelly, or mineral oil. The lubricant may be present in the precursor in an amount of from about 0.1 weight % to about 10 weight percent based on the weight of the composition, preferably from about 0.5 weight % to about 5 weight % based on the weight of the composition, and more preferably from about 1 weight % to about 3 weight % based on the weight of the composition. The amounts of the components to be used are to some extent interdependent and will depend on a number of factors that relate to the equipment used. However these matters are well within the general knowledge of a person skilled in the art of extruding ceramic materials. Preparation of a catalyst carrier generally uses a step of kneading the precursor material into a desired shape and a desired size. The catalyst support particles are then formed from the paste by conventional means such as, for example, pelletizing, high pressure extrusion, granulation or other ceramic forming processes. For use in commercial ethylene oxide production applications, the supports are desirably formed into regularly shaped pellets, spheres, rings, particles, chunks, pieces, wagon wheels, cylinders, trilobes, tetralobes and the like of a size suitable for employment in fixed bed reactors. Desirably, the support particles may have "equivalent diameters" in the range of from about 3 mm to about 20 mm and preferably in the range of from about 4 mm to about 12 mm, which are usually compatible with the internal diameter of the tube reactors in which the catalyst is placed. "Equivalent diameter" is the diameter of a sphere having the same external surface (i.e. neglecting surface within the pores of the particle) to volume ratio as the support particles being employed. The particles are then dried and are subsequently fired at an elevated temperature. The function of the drying step is to remove the water from the shaped pellets. The formed carrier precursor is dried to at a temperature of from about 80° C. to about 150° C. for a time sufficient to remove substantially all of the water. Then the extruded material is calcined under conditions sufficient to remove the burnout agents and the organic binding agents and to fuse the alpha alumina particles into a porous, hard mass. The carrier is heated at a temperature that is high enough to sinter the alumina particles and produce a structure with physical properties adequate to withstand the environment in which it is expected to operate. The calcination temperature and duration should be high enough to convert any transition alumina into alpha alumina and to induce grain boundary fusion. Controlling the calcination process is essential to obtain a carrier having the optimum balance between surface area, porosity and strength. Typically the calcination temperature is higher than 1000° C., preferably is in the range of 1150° C. to about 1600° C. The holding times at these maximum temperatures typically range from about 0 hour to 10 hours, preferably from about 0.1 hour to about 10 hours preferably from about 0.2 hour to about 5 hours to form the support.

The final carrier has a water pore volume ranging from about 0.2 cc/g to about 0.8 cc/g, preferably from about 0.25 cc/g to about 0.6 cc/g. The BET surface area of the finished carrier is preferred to be in the range of 0.4-4.0 m$^2$/g, more preferably from about 0.6 to about 1.5 m$^2$/g. The suitable value of crush strength is about 8 pounds and higher, preferably about 10 pounds and higher, and more preferably about 14 pounds and higher. Suitable porosity is expected to be in the range of from about 20 to about 80%, preferably from about 25 to about 50%.

In another embodiment of the invention, the catalyst support is prepared as above except the composition comprises talc instead of or in addition to the permanent binder component. The talc may be present in the precursor in an amount of from about 0.1 weight % to about 15 weight % based on the weight of the composition, preferably from about 0.5 weight % to about 10 weight % based on the weight of the composition, and more preferably from about 1 weight % to about 8 weight % based on the weight of the composition. The support is then formed in a manner similar to that described above.

In another embodiment of the invention, the support is prepared as above except the composition comprises a water soluble titanium compound instead of or in addition to the permanent binder. Suitable water soluble titanium compounds non-exclusively include ammonium hexafluorotitanate, titanyl oxalate, and titanium (IV) bis(ammonium lactato) dihydroxide. The water soluble titanium compound may be present in the precursor in an amount of from about 0.01 weight % to about 10 weight percent based on the weight of the composition, preferably from about 0.1 weight % to about 8 weight percent based on the weight of the composition, and more preferably from about 0.2 weight % to about 5 weight percent based on the weight of the composition. The support is then formed in a manner similar to that described above. The optional addition of a small amount of boron, added as boric acid or a borate, also gives good results. The amount of boron added is in the range of 0.0 to 3% based on the dry weight of the alumina used.

In order to produce a catalyst for the oxidation of ethylene to ethylene oxide, a support formed above is then provided with a catalytically effective amount of silver thereon. The catalysts are prepared by impregnating the supports with silver ions, compounds, complexes and/or salts dissolved in a suitable solvent sufficient to cause deposition of silver precursor compound onto the support. The impregnated carrier is then removed from the solution and the deposited silver compound is reduced to metallic silver by high temperature calcination. Also preferably deposited on the support either prior to, coincidentally with, or subsequent to the deposition of the silver are suitable promoters in the form of ions, compounds and/or salts of an alkali metal dissolved in a suitable solvent. Also deposited on the carrier either prior to, coincidentally with, or subsequent to the deposition of the silver and/or alkali metal, suitable transition metal compounds, complexes and/or salts dissolved in an appropriate solvent.

The supports as formed above are impregnated with a silver impregnating solution, preferably an aqueous silver solution. The support is also impregnated at the same time or in a separate step with various catalyst promoters. Preferred catalysts prepared in accordance with this invention contain up to about 45% by weight of silver, expressed as metal, deposited upon the surface and throughout the pores of a porous support. Silver contents, expressed as metal, of from about 1 to about 40% based on weight of total catalyst are preferred, while silver contents of from about 8 to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide and selectivity and activity stability within catalyst life. Useful silver containing compounds non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

This catalyst comprises a catalytically effective amount of silver, a promoting amount of alkali metal, a promoting amount of a transition metal supported on a porous, support. As used herein the term "promoting amount" of a certain component of a catalyst refers to an amount of that component that works effectively to provide an improvement in one or more of the catalytic properties of that catalyst when compared to a catalyst not containing said component. The exact concentrations employed, of course, will depend upon, among other factors, the desired silver content, the nature of the support, the viscosity of the liquid, and solubility of the silver compound.

In addition to silver, the catalyst also contains an alkali metal promoter selected from lithium, sodium, potassium, rubidium, cesium or combinations thereof, with, cesium being preferred. The amount of alkali metal deposited on the support or catalyst or present on the support or catalyst is to be a promoting amount. Preferably the amount will range from about 10 ppm to about 3000 ppm, more preferably from about 50 ppm to about 2000 ppm and even more preferably from about 100 ppm to about 1500 ppm and yet even more preferably from about 200 ppm to about 1000 ppm by weight of the total catalyst, measured as the metal.

The catalyst also preferably contains a transition metal promoter which comprises an element from Groups 4b, 5b, 6b, 7b and 8 of the Periodic Table of the Elements, and combinations thereof. Preferably the transition metal comprises an element selected from Group 6b, and 7b of the Periodic Table of the Elements. More preferred transition metals are rhenium, molybdenum, and tungsten, with molybdenum and rhenium most preferred. The amount of transition metal promoter deposited on the support or catalyst or present on the support or catalyst is to be a promoting amount. The transition metal promoter may be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal.

The silver solution used to impregnate the support may also comprise an optional solvent or complexing/solubilizing agent, such as are known in the art. A wide variety of solvents or complexing/solubilizing agents may be employed to solubilize silver to the desired concentration in the impregnating medium. Useful complexing/solubilizing agents include amines, ammonia, or lactic acid. Amines include alkylene diamines, and alkanol amines having from 1 to 5 carbon atoms. In one preferred embodiment, the solution comprises an aqueous solution of silver oxalate and ethylene diamine. The complexing/solubilizing agent may be present in the impregnating solution in an amount of from about 0.1 to about 5.0 moles of ethylene diamine per mole of silver, preferably from about 0.2 to about 4.0 moles, and more preferably from about 0.3 to about 3.0 moles of ethylene diamine for each mole of silver.

When a solvent is used it may be water-based, or organic-based, and may be polar or substantially or totally non-polar. In general, the solvent should have sufficient solvating power to solubilize the solution components. At the same time, it is preferred that the solvent be chosen to avoid having an undue influence on or interaction with the solvated promoters. The concentration of silver salt in the solution is in the range of from about 1% by weight to the maximum permitted by the solubility of the particular salt/solubilizing agent combination employed. It is generally very suitable to employ silver salts solutions containing from 5% to about 45% by weight of silver with silver salt concentrations of from 10 to 35% by weight being preferred.

Impregnation of the selected support is achieved in conventional manners by excess solution impregnation, incipient wetness, etc. Typically the support material is placed in the silver solution until a sufficient amount of the solution is absorbed by the support. Preferably the quantity of the silver solution used to impregnate the porous support is no more than is necessary to fill the pore volume of the support. The silver containing liquid penetrates by absorption, capillary action and/or vacuum into the pores of the support. A single impregnation or a series of impregnations, with or without intermediate drying, may be used, depending in part on the concentration of the silver salt in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888, which are incorporated herein by reference. Known prior procedures of pre-deposition, co-deposition and post-deposition of various promoters can be employed.

Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to optimize conditions and results by taking into account feedstock costs, energy costs, by-product removal costs and the like. The particular combination of silver, support, alkali metal promoter, and transition metal promoter of the instant invention will provide an improvement in one or more catalytic properties over the same combination of silver and support and none, or only one promoter.

After impregnation, the support impregnated with silver precursor compound and the promoters is calcined or activated, for a time sufficient to reduce the silver component to metallic silver and to remove the solvent and volatile decomposition products from the silver containing support. The calcination is accomplished by heating the impregnated support, preferably at a gradual rate, to a temperature in the range of from about 200° C. to about 600° C., preferably from about 230° C. to about 500° C., and more preferably from about 250° C. to about 450° C., at a reaction pressures in the range of from 0.5 to 35 bar, for a time sufficient to convert the contained silver to silver metal and to decompose all or substantially all of present organic materials and remove the same as volatiles. In general, the higher the temperature, the shorter the required calcination period. A wide range of heating periods have been suggested in the art to thermally treat the impregnated support, e.g., U.S. Pat. No. 3,563,914 suggests heating for less than 300 seconds, U.S. Pat. No. 3,702,259 discloses heating from 2 to 8 hours at a temperature of from 100° C. to 375° C. to reduce the silver salt in the catalyst; usually for from about 0.5 to about 8 hours, however, it is only important that the reduction time be correlated with temperature such that substantially complete reduction of silver salt to catalytically active metal is accomplished. A continuous or step-wise heating program may be used for this purpose.

The impregnated support is maintained under an atmosphere comprising an inert gas and optionally an oxygen containing oxidizing component. In one embodiment the oxidizing component is present in an amount of from about 10 ppm to about 5% by volume of gas. For purposes of this invention, inert gases are defined as those which do not substantially react with the catalyst producing components under the catalyst preparation conditions chosen. These include nitrogen, argon, krypton, helium, and combinations thereof, with the preferred inert gas being nitrogen. In a useful embodiment, the atmosphere comprises from about 10 ppm to about 1% by volume of a gas of an oxygen containing oxidizing component. In another useful embodiment, the atmosphere comprises from about 50 ppm to about 500 ppm of a gas of an oxygen containing oxidizing component.

Ethylene Oxide Production

Generally, the commercially practiced ethylene oxide production processes are carried out by continuously contacting an oxygen containing gas with ethylene in the presence of the present catalysts at a temperature in the range of from about 180° C. to about 330° C. and preferably about 200° C. to about 325° C., more preferably from about 210° C. to about 270° C., at a pressure which may vary from about atmospheric pressure to about 30 atmospheres depending on the mass velocity and productivity desired. Higher pressures may, however, be employed within the scope of the invention. Residence times in large-scale reactors are generally on the order of about 0.1-5 seconds. Oxygen may be supplied to the reaction in an oxygen containing stream, such as air or as commercial oxygen. The resulting ethylene oxide is separated and recovered from the reaction products using conventional methods. However, for this invention, the ethylene oxide process envisions the normal gas recycle encompassing carbon dioxide recycle in the normal concentrations, e.g., about 0.1-15 volume percent. A usual process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalysts of the present invention broadly comprise those described in the prior art. This applies, for example, to suitable temperatures, pressures, residence times, diluent materials such as nitrogen, carbon dioxide, steam, argon, methane, the presence or absence of moderating agents to control the catalytic action, for example, ethyl chloride, 1,2-dichloroethane, or vinyl chloride, the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, a concentrated oxygen stream comprising oxygen in major amount with lesser amounts of one or more diluents such as nitrogen, argon, etc., or another oxygen containing stream such as air. The use of the present catalysts in ethylene oxidation reactions is in no way limited to the use of specific conditions among those which are known to be effective.

The resulting ethylene oxide is separated and recovered from the reaction products by conventional methods known and used in the art. Use of the silver catalysts of the invention in ethylene oxide production processes gives higher overall ethylene oxidation selectivities to ethylene oxide at a given ethylene conversion than are possible with conventional catalysts.

In the production of ethylene oxide, reactant feed mixtures may contain 0.5 to 45% ethylene and 3 to 15% oxygen, with the balance comprising comparatively inert materials including such substances as nitrogen, carbon dioxide, methane, ethane, argon and the like. In a preferred application of the silver catalysts of the invention ethylene oxide is produced when an oxygen containing gas of about 95% or more of oxygen. Only a portion of the ethylene usually is reacted per pass over the catalyst and after separation of the desired ethylene oxide product and the removal of appropriate purge stream and carbon dioxide to prevent uncontrolled build up of inerts and/or by-products, unreacted materials are returned to the oxidation reactor. For purposes of illustration only, the following are conditions that are often used in current commercial ethylene oxide reactor units. GHSV—1500-10,000; Inlet pressure—150-400 psig; Inlet Feed: ethylene 1-40%; $O_2$—3-12%; $CO_2$—0.1-40%; ethane 0-3%; argon and/or methane and/or nitrogen argon and/or methane and/or nitrogen: 0.3-20 ppmv total diluent chlorohydrocarbon moderator; coolant temperature—180-315° C.; catalyst temperature 180° C.; $O_2$ conversion level—10-60%; EO Production (Work Rate) 2-16 lbs. EO/cu.ft. catalyst/hr.

The following non-limiting examples serve to illustrate the invention.

EXAMPLE 1

The following components were mixed thoroughly:

| | |
|---|---|
| 100 g | alpha alumina(I)* |
| 120 g | alpha alumina(II)** |
| 290 g | Hydrated alumina (Gibssite) |
| 60 g | Boehmite |
| 14 g | K15M Methocel (methyl cellulose) |
| 2 g | *Acacia* |
| 94 g | polycarbonate powder |
| 25 g | Mineral oil |
| 8 g | 50% Ti solution (as titanium bis-ammonium lactato dihydroxide) |
| 30 | Talc |
| 143 g | Water |

*Alpha Alumina(I) is a highly pure alpha alumina that has a BET surface area of 0.7 $m^2$/g and Na contents of less than 0.3%.
**Alpha Alumina(II) is a highly pure alpha alumina that has a BET surface area of 11 $m^2$/g and Na contents of less than 0.15%.

Step 1

All the dry components were mixed together, in a dry powder mixer (US Stoneware Model M93120DC). The dry mixture was transferred to a high shear mixer (Lancaster Model 530PO). There it was blended with the water and the water-soluble components and mixing continued for 15 more minutes.

Step 2

The plastic mixture was extruded into 8 mm hollow cylinders, using a Killion extruder (Model 4321111282).

Step 3

The shaped pellets were dried at 120° C. and this was followed by firing in a slow and programmed scheme. The firing process involved heating the green ware in a high temperature furnace, using a CM furnace (Model 1720). The firing scheme involved temperature ramping at a rate of 4° C./min up to 1275° C. The temperature of the furnace was held at this level for 2 hours and then it was allowed to cool down at a rate of 6° C./min. This carrier is designated as carrier A. Testing the carrier showed that it has the following specifications:

Testing the carrier showed that it has the following specifications:

| | |
|---|---|
| Crush strength | 19.2 lb |
| Water absorption | 32.3 ml/100 g |
| BET surface area | 1.03 $m^2$/g |

EXAMPLE 2

The following components were mixed thoroughly:

| | |
|---|---|
| 176 g | alpha alumina(II)** |
| 232 g | Hydrated alumina (Gibssite) |
| 48 g | Boehmite |
| 15 g | K15M Methocel (methyl cellulose) |
| 2 g | *Acacia* |
| 80 g | azodicarbonamide |
| 20 g | mineral oil |
| 6.2 g | 50% Ti solution (as titanium bis-ammonium lactato dihydroxide) |
| 16 g | Talc |
| 105 g | Water |

Mixing, shaping, and drying these components followed the same procedure as in Example 1. The firing scheme involved temperature ramping at a rate of 4° C./min. up to 1350° C. The temperature of the furnace was then held at this level for 2 hours before it was allowed to cool down at a rate of 5° C./min. This carrier is designated as carrier B. Testing the carrier showed that it has the following specifications:

| | |
|---|---|
| Crush strength | 17.4 lb |
| Water absorption | 29.6 ml/100 g |
| BET surface area | 1.03 $m^2$/g |

EXAMPLE 3

The following components were mixed thoroughly:

| | |
|---|---|
| 240 g | alpha alumina(I)* |
| 200 g | alpha alumina(II)** |
| 580 g | Hydrated alumina (Gibssite) |
| 120 g | Boehmite |
| 28 g | A4 Methocel (methyl cellulose) |
| 94 g | Polycarbonate powder |
| 50 g | mineral oil |
| 15.6 g | 50% Ti solution (as titanium bis-ammonium lactato dihydroxide) |
| 40 g | Talc |
| 216 g | Water |

Mixing, shaping, and drying these components followed the same procedure as in Example 1. The firing scheme involved temperature ramping at a rate of 4° C./min. up to 1350° C. The temperature of the furnace was then held at this level for 2 hours before it was allowed to cool down at a rate of 5° C./min. This carrier is designated as carrier C. Testing the carrier showed that it has the following specifications:

| | |
|---|---|
| Crush strength | 19.4 lb |
| Water absorption | 31.7 ml/100 g |
| BET surface area | 1.01 $m^2$/g |

EXAMPLE 4

The following components were mixed thoroughly:

| | |
|---|---|
| 176 g | alpha alumina(II)** |
| 232 g | Hydrated alumina (Gibssite) |
| 48 g | Boehmite |
| 12 g | K15M Methocel (methyl cellulose) |

|       |                                                              |
|-------|--------------------------------------------------------------|
| 30 g  | powdered walnut shells                                       |
| 20 g  | Mineral oil                                                  |
| 6.2 g | 50% Ti solution                                              |
|       | (as titanium bis-ammonium lactato dihydroxide)               |
| 16    | Talc                                                         |
| 108 g | Water                                                        |

Mixing, shaping, and drying these components followed the same procedure as in Example 1. The firing scheme involved temperature ramping at a rate of 4° C./min. up to 1350° C. The temperature of the furnace was then held at this level for 2 hours before it was allowed to cool down at a rate of 5° C./min. Testing the carrier showed that it has the following specifications:

| Crush strength  | 15.4 lb                |
|-----------------|------------------------|
| Water absorption| 30.6 ml/100 g          |
| BET surface area| 0.93 m$^2$/g           |

EXAMPLE 5

The following components were mixed thoroughly:

|        |                                                              |
|--------|--------------------------------------------------------------|
| 220 g  | alpha alumina(II)**                                          |
| 282 g  | Boehmite                                                     |
| 15 g   | K15M Methocel (methyl cellulose)                             |
| 50 g   | Polycarbonate powder                                         |
| 25 g   | Mineral oil                                                  |
| 7.8    | 50% Ti solution                                              |
|        | (as titanium bis-ammonium lactato dihydroxide)               |
| 20     | Talc                                                         |
| 108 g  | Water                                                        |

Mixing, shaping, and drying these components followed the same procedure as in Example 1. The firing scheme involved temperature ramping at a rate of 4° C./min. up to 1350° C. The temperature of the furnace was then held at this level for 2 hours before it was allowed to cool down at a rate of 5° C./min. This carrier is designated as carrier D. Testing the carrier showed that it has the following specifications:

| Crush strength  | 14.5 lb                |
|-----------------|------------------------|
| Water absorption| 32.2 ml/100 g          |
| BET surface area| 1.19 m$^2$/g           |

EXAMPLE 6

The following components were mixed thoroughly:

|        |                                      |
|--------|--------------------------------------|
| 220 g  | alpha alumina(II)**                  |
| 290 g  | Hydrated alumina (Gibssite)          |
| 60 g   | Boehmite                             |
| 15 g   | K15M Methocel (methyl cellulose)     |
| 50 g   | Polycarbonate powder                 |
| 25 g   | Mineral oil                          |
| 20     | Talc                                 |
| 115 g  | Water                                |

Mixing, shaping, and drying these components followed the same procedure as in Example 1. The firing scheme involved temperature ramping at a rate of 4° C./min. up to 1350° C. The temperature of the furnace was then held at this level for 2 hours before it was allowed to cool down at a rate of 5° C./min. This carrier is designated as carrier E. Testing the carrier showed that it has the following specifications:

| Crush strength  | 21.9 lb                |
|-----------------|------------------------|
| Water absorption| 30.5 ml/100 g          |
| BET surface area| 1.19 m$^2$/g           |

EXAMPLE 7

The following components were mixed thoroughly:

|        |                                                              |
|--------|--------------------------------------------------------------|
| 510 g  | Hydrated alumina (Gibssite)                                  |
| 195 g  | Boehmite                                                     |
| 15 g   | K15M Methocel (methyl cellulose)                             |
| 75 g   | Polycarbonate powder                                         |
| 25 g   | Mineral oil                                                  |
| 8 g    | 50% Ti solution                                              |
|        | (as titanium bis-ammonium lactato dihydroxide)               |
| 20 g   | Talc                                                         |
| 10 g   | ammonium fluoride                                            |
| 195 g  | Water                                                        |

Mixing, shaping, and drying these components followed the same procedure as in Example 1. The firing scheme involved temperature ramping at a rate of 4° C./min. up to 1250° C. The temperature of the furnace was then held at this level for 2 hours before it was allowed to cool down at a rate of 5° C./min. This carrier is designated as carrier F. Testing the carrier showed that it has the following specifications:

| Crush strength  | 20.5 lb                |
|-----------------|------------------------|
| Water absorption| 73.7 ml/100 g          |
| BET surface area| 0.91 m$^2$/g           |

EXAMPLE 8

The following components were mixed thoroughly:

|         |                                                              |
|---------|--------------------------------------------------------------|
| 389 g   | Hydrated alumina (Gibssite)                                  |
| 111 g   | Boehmite                                                     |
| 18 g    | K15M Methocel (methyl cellulose)                             |
| 5 g     | EXPANCEL 551                                                 |
| 25.0 g  | mineral oil                                                  |
| 7.8 g   | 50% Ti solution                                              |
|         | (as titanium bis-ammonium lactato dihydroxide)               |
| 20 g    | Talc                                                         |
| 108 g   | Water                                                        |

Mixing, shaping, and drying these components followed the same procedure as in Example 1. The firing scheme involved temperature ramping at a rate of 4° C./min. up to 1375° C. The temperature of the furnace was then held at this level for 2 hours before it was allowed to cool down at a rate of 5° C./min. This carrier is designated as carrier G. Testing the carrier showed that it has the following specifications:

| Crush strength  | 14.8 lb                |
|-----------------|------------------------|
| Water absorption| 33.0 ml/100 g          |
| BET surface area| 1.27 m$^2$/g           |

EXAMPLE 9

The following components were mixed thoroughly:

| | |
|---|---|
| 60 g | alpha alumina(I)* |
| 60 g | alpha alumina(II)** |
| 280 g | Hydrated alumina (Gibssite) |
| 80 g | Boehmite |
| 28 g | K15M Methocel (methyl cellulose) |
| 5 g | Expancel 551 |
| 25 g | mineral oil |
| 7.8 g | 50% Ti solution |
| | (as titanium bis-ammonium lactato dihydroxide) |
| 20 g | Talc |
| 108 g | Water |

Mixing, shaping, and drying these components followed the same procedure as in Example 1. The firing scheme involved temperature ramping at a rate of 4° C./min. up to 1325° C. The temperature of the furnace was then held at this level for 2 hours before it was allowed to cool down at a rate of 5° C./min. This carrier is designated as carrier H. Testing the carrier showed that it has the following specifications:

| | |
|---|---|
| Crush strength | 23.8 lb |
| Water absorption | 31.2 ml/100 g |
| BET surface area | 1.28 m$^2$/g |

EXAMPLE 10

The following components were mixed thoroughly:

| | |
|---|---|
| 170 g | alpha alumina(II)** |
| 333 g | Hydrated alumina (Gibssite) |
| 167 g | Boehmite |
| 15 g | K15M Methocel (methyl cellulose) |
| 75 g | Polycarbonate powder |
| 25.0 g | mineral oil |
| 8 g | 50% Ti solution |
| | (as titanium bis-ammonium lactato dihydroxide) |
| 20 g | Clay (hydrous aluminum silicate) |
| 120 g | Water |

Mixing, shaping, and drying these components followed the same procedure as in Example 1. The firing scheme involved temperature ramping at a rate of 4° C./min. up to 1375° C. The temperature of the furnace was then held at this level for 2 hours before it was allowed to cool down at a rate of 5° C./min. Testing the carrier showed that it has the following specifications:

| | |
|---|---|
| Crush strength | 12.7 lb |
| Water absorption | 58.0 ml/100 g |
| BET surface area | 0.72 m$^2$/g |

EXAMPLE 11 a. Preparation of a Stock Solution of Silver/Amine Complex:

A silver solution was prepared using the following components (parts are by weight):

| | |
|---|---|
| Silver oxide | 834 parts |
| Oxalic acid | 442 parts |
| De-ionized water | 2808 parts |
| Ethylenediamine | 415 parts |

Silver oxide was mixed with water, at room temperature, followed by the gradual addition of the oxalic acid. The mixture was stirred for 15 minutes and at that point, the color of the black suspension of silver oxide had changed to the light brown color of silver oxalate. The mixture was filtered and the solids were washed with 3 liters of de-ionized water.

The sample was placed in an ice bath and stirred while ethylenediamine and water (as a 66%/34% mixture) were added slowly in order to maintain the reaction temperature lower than 33° C. After the addition of all the ethylenediamine/water mixture, the solution was filtered at room temperature. The clear filtrate was utilized as a silver/amine stock solution for the catalyst preparation.

b. Promoters Addition:

The clear stock solution was diluted with the 66/34 mixture of ethylenediamine/water. In addition, Cs hydroxide and ammonium hydrogen sulfate were added to the diluted silver solution in order to prepare a catalyst containing 11% silver, and the suitable amount of cesium and sulfur.

c. Catalyst Impregnation:

A 150 g sample of the carrier was placed in a pressure vessel and then exposed to vacuum until the pressure was reduced to 50 mm Hg. 200 ml of the adjusted silver/promoters solution was introduced to the flask while it is still under vacuum. The pressure of the vessel was allowed to rise to atmospheric pressure and its contents were shaken for few minutes. The catalyst was separated from the solution and was now ready for calcination.

d. Catalyst Calcination:

Calcination, deposition of silver, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. It was increased, up to 400° C., as the catalyst passed through seven heating zones. After the heating zones, the belt passed through a cooling zone that gradually cooled the catalyst to a temperature lower than 100° C. The total residence time in the furnace was 22 minutes. The atmosphere of the furnace was controlled through the use of nitrogen flow in the different heating zones. This catalyst is designated as catalyst 3.

c. Catalyst Testing:

The catalysts were tested in a stainless steel tube that was heated by a molten salt bath. A gas feed mixture containing 15% ethylene, 7% oxygen, and 78% inert, mainly nitrogen and carbon dioxide, was used to test the catalyst at 300 p.s.i.g. The temperature of the reaction was adjusted in order to obtain a standard ethylene oxide productivity of 160 Kg per hour per m³ of catalyst.

EXAMPLE 12

Carriers A-H were used to prepare catalysts for the oxidation of ethylene to ethylene oxide in a procedure illustrated in Example 11. The results of the catalyst testing are summarized in Table 1.

TABLE 1

Results of catalyst testing

| Catalyst | Carrier | Selectivity | Reaction Temp ° C. |
|---|---|---|---|
| 12-a | A | 83.7 | 237 |
| 12-b | B | 82.9 | 227 |
| 12-c | C | 84.2 | 239 |
| 12-d | D | 82.9 | 227 |
| 12-e | E | 82.2 | 231 |
| 12-f | F | 81.9 | 244 |
| 12-g | G | 84.2 | 230 |
| 12-h | H | 84.3 | 232 |

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A composition for producing an alpha alumina catalyst support, the composition comprising at least one alpha alumina having a median particle size of at least 5 microns, in an amount of about 20 percent to about 60 percent by weight of total alumina in the composition; at least one hydrated precursor of alpha alumina in an amount of about 40 percent to about 80 percent by weight of total alumina in the composition; and a binder, wherein the composition is substantially free of seeding particles.

2. The composition of claim 1, wherein the composition is free of seeding particles.

3. The composition of claim 1, wherein the at least one hydrated precursor of alpha alumina comprises an aluminum hydroxide.

4. The composition of claim 3, wherein the aluminum hydroxide is selected from the group consisting of gibbsite, boehmite, diaspore, bayerite, and combinations thereof.

5. The composition of claim 1, wherein the composition is substantially free of ferric oxide, chromium oxide, and sub-micron size particles of alpha alumina.

6. The composition of claim 1, further comprising water in an amount sufficient to render the composition extrudable.

7. The composition of claim 1, wherein the binder comprises a material selected from the group consisting of thermally decomposable organic compounds, clays, silica, silicates of elements of Group II of the Periodic Table of the elements, and combinations thereof.

8. The composition of claim 1, wherein the binder comprises a material selected from the group consisting of polyolefin oxides, oil, acacia, carbonaceous materials, cellulose, substituted celluloses, cellulose ether, stearates, waxes, granulated polyolefins, polystyrene, polycarbonate, sawdust, ground nut shell flour, silica, an alkali metal salt, and combinations thereof.

9. The composition of claim 1, wherein the composition further comprises talc.

10. The composition of claim 1, wherein the composition further comprises a water-soluble titanium compound.

11. The composition of claim 1, wherein the composition further comprises a burnout material.

12. The composition of claim 1, wherein the composition further comprises a blowing agent.

13. The composition of claim 12, wherein the blowing agent propels a gas upon the application of sufficient heat.

14. The composition of claim 1, wherein the composition further comprises boron.

15. A process for producing an alpha alumina catalyst support, the process comprising:
    a) preparing a composition comprising at least one alpha alumina having a median particle size of at least 5 microns, in an amount of about 20 percent to about 60 percent by weight of total alumina in the composition; at least one hydrated precursor of alpha alumina in an amount of about 40 percent to about 80 percent by weight of total alumina in the composition; and a binder, wherein the composition is substantially free of seeding particles;
    b) molding the composition into a structure;
    c) heating said structure for a sufficient time and at a sufficient temperature to form a porous structure; and
    d) calcining the porous structure at a temperature above 1000° C. for a sufficient time to convert the at least one hydrated precursor of alpha alumina to a porous and fused alpha alumina structure.

16. The process of claim 15, wherein step c), step d), or both step c) and step d), are conducted in an atmosphere of an inert gas.

17. A process for producing a catalyst, the process comprising producing an alpha alumina catalyst support according to claim 15, and then e) depositing a catalytically effective amount of silver onto a surface of said catalyst support.

18. The process of claim 17, further comprising depositing a promoting amount of a promoter onto the surface of the catalyst support, the promoter comprising one or more alkali metal-containing compounds, one or more transition metal-containing compounds, one or more sulfur components, one or more fluorine-containing components, or a combination thereof.

19. A process for the oxidation of ethylene to ethylene oxide, the process comprising vapor phase oxidation of ethylene with molecular oxygen in a fixed bed tubular reactor in the presence of the catalyst produced by the process of claim 17.

20. The catalyst produced by the process of claim 18.

21. The composition of claim 1, wherein said at least one hydrated precursor of alpha alumina is in an amount of about 75 percent to about 80 percent by weight of total alumina in the composition.

* * * * *